US011583419B2

(12) United States Patent
Palagi et al.

(10) Patent No.: US 11,583,419 B2
(45) Date of Patent: *Feb. 21, 2023

(54) STEERABLE IMPLANT, INSTALLER, AND METHOD OF INSTALLATION

(71) Applicant: Life Spine, Inc., Huntley, IL (US)

(72) Inventors: Gregory Palagi, Geneva, IL (US); Eugene Shoshtaev, Del Mar, CA (US); Madeline C. Wolters, St. Charles, IL (US); David T. Mehl, Lake in the Hills, IL (US); Daniel P. Predick, West Lafayette, IN (US); Casey Rice, Woodstock, IL (US)

(73) Assignee: LifeSpine, Inc., Huntley, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/466,255

(22) Filed: Sep. 3, 2021

(65) Prior Publication Data

US 2021/0401588 A1   Dec. 30, 2021

Related U.S. Application Data

(63) Continuation of application No. 16/360,539, filed on Mar. 21, 2019, now Pat. No. 11,109,983, which is a
(Continued)

(51) Int. Cl.
*A61F 2/46* (2006.01)
*A61F 2/44* (2006.01)
*A61F 2/30* (2006.01)

(52) U.S. Cl.
CPC ............ *A61F 2/4611* (2013.01); *A61F 2/447* (2013.01); *A61F 2/4465* (2013.01);
(Continued)

(58) Field of Classification Search
None
See application file for complete search history.

(56) References Cited

U.S. PATENT DOCUMENTS 9,198,772 B2   12/2015   Weiman
9,204,972 B2   12/2015   Weiman et al.
(Continued)

FOREIGN PATENT DOCUMENTS

EP   2 535 021 A1   12/2012

OTHER PUBLICATIONS

International Search Report and Written Opinion on PCT/US2018/028452 dated Jun. 22, 2018 (12 pages).
(Continued)

*Primary Examiner* — Tessa M Matthews
(74) *Attorney, Agent, or Firm* — Foley & Lardner LLP

(57) ABSTRACT

A spine implant for a TLIF surgical procedure is configured to be guided into place during implantation in conjunction with a complementary insertion instrument. The cage of the implant is constrained to a limited range of rotation about a pivoting post carried by the cage. The insertion instrument is configured to hold the post while controllably rotating the cage relative to the post in order to angularly position the implant during implantation. Range of rotational motion is controlled by the configuration of an opening in and end of the cage and a groove in the pivot post. A retaining pin of the implant extends from the cage into the groove of the post to rotationally connect the cage to the post.

19 Claims, 16 Drawing Sheets

Related U.S. Application Data continuation-in-part of application No. 15/957,893, filed on Apr. 19, 2018, now Pat. No. 10,617,534.

(60) Provisional application No. 62/646,067, filed on Mar. 21, 2018.

(52) U.S. Cl.
CPC ............ *A61F 2002/3092* (2013.01); *A61F 2002/30143* (2013.01); *A61F 2002/30266* (2013.01); *A61F 2002/30593* (2013.01); *A61F 2002/30622* (2013.01); *A61F 2002/30784* (2013.01); *A61F 2002/4628* (2013.01); *A61F 2002/4629* (2013.01)

(56) References Cited

U.S. PATENT DOCUMENTS

| | | |
|---|---|---|
| 9,554,918 B2 | 1/2017 | Weiman |
| 9,770,343 B2 | 9/2017 | Weiman |
| 9,931,226 B2 | 4/2018 | Kurtaliaj et al. |
| 9,968,462 B2 | 5/2018 | Weiman |
| 10,004,607 B2 | 6/2018 | Weiman et al. |
| 10,765,528 B2 | 9/2020 | Weiman et al. |
| 10,874,522 B2 | 12/2020 | Weiman |
| 10,874,523 B2 | 12/2020 | Weiman et al. |
| 11,109,983 B2 * | 9/2021 | Palagi .................. A61F 2/4611 |
| 2009/0276049 A1 | 11/2009 | Weiland |
| 2010/0256759 A1 | 10/2010 | Hansell et al. |
| 2010/0256760 A1 | 10/2010 | Hansell |
| 2011/0276142 A1 | 11/2011 | Niemiec et al. |
| 2013/0096685 A1 | 4/2013 | Ciupik et al. |
| 2013/0103102 A1 | 4/2013 | Taylor et al. |
| 2014/0058513 A1 | 2/2014 | Gahman et al. |
| 2016/0045333 A1 | 2/2016 | Baynham |
| 2016/0113776 A1 | 4/2016 | Capote |

OTHER PUBLICATIONS

International Search Report and Written Opinion on PCT/US2019/023446 dated Jun. 17, 2019 (16 pages).

\* cited by examiner

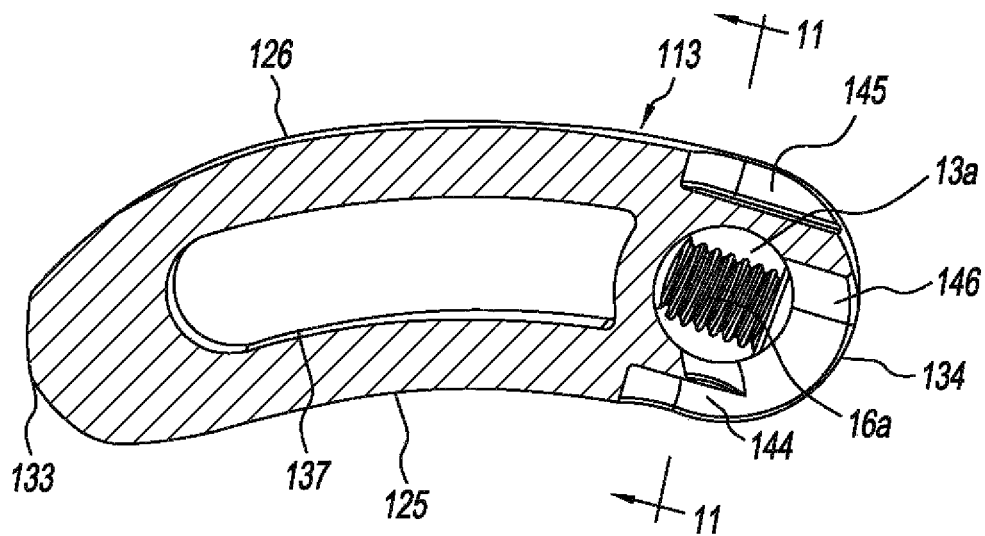
Fig. 10
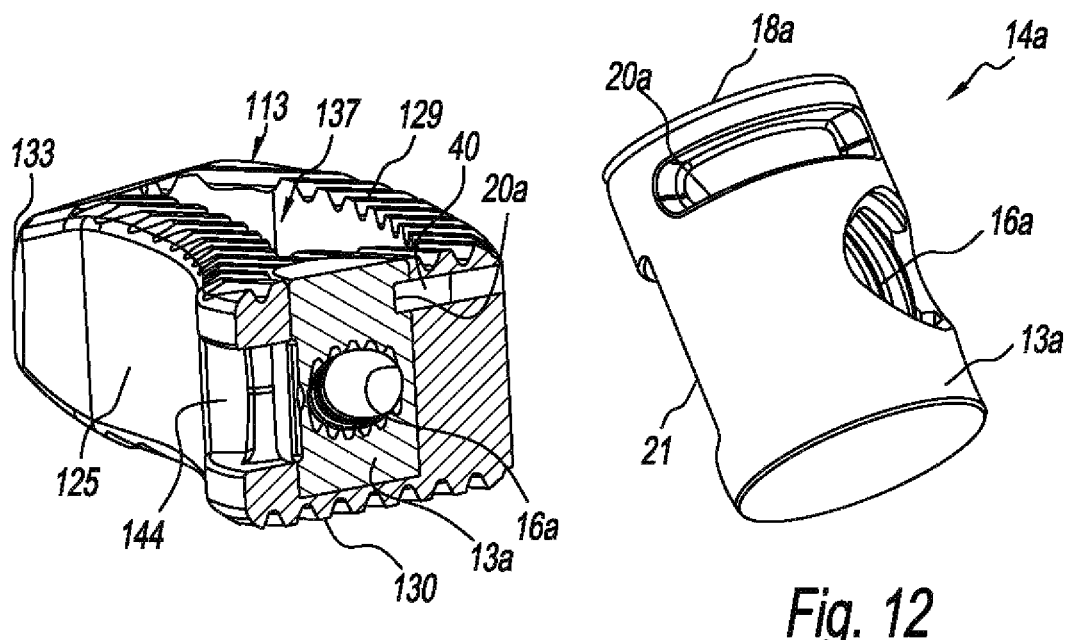
Fig. 11
Fig. 12

STEERABLE IMPLANT, INSTALLER, AND METHOD OF INSTALLATION

CROSS-REFERENCE TO RELATED APPLICATIONS

This U.S. non-provisional patent application is a continuation of U.S. application Ser. No. 16/360,539 filed on Mar. 21, 2019, which is a continuation-in-part of U.S. application Ser. No. 15/957,893 filed Apr. 19, 2018, and also claims the benefit of and/or priority under 35 U.S.C. § 119(e) to U.S. provisional App. No. 62/646,067 filed Mar. 21, 2018, the entire contents of each of which is specifically incorporated herein by reference.

BACKGROUND

The present invention relates to methods and devices for orthopedic surgery of the spine such as vertebral fusion and, particularly, to devices and methods for transforaminal lumbar interbody fusion (TLIF).

Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

Vertebral fusion of the spine, such as in the lumbar region (a lumbar fusion), may be accomplished using several techniques. Once such technique is known as a transforaminal lumbar interbody fusion or TLIF. TLIF spine surgery is performed through the posterior aspect of the spine and provides stabilization of the anterior portion by an interbody cage and bone graft while the posterior portion is locked in place with pedicle screws, rods and bone graft. A TLIF procedure is advantageous over a posterior lumbar interbody fusion (PLIF) and other lumbar fusion procedures for several reasons. In a TLIF procedure, bone fusion is enhanced because bone graft is not only placed along the "gutters" of the spine posteriorly, but also in the disc space. A TLIF procedure also allows the surgeon to insert bone graft and an interbody cage into the disc space laterally from a unilateral approach without forcefully retracting the nerve roots as much as the PLIF approach, which can reduce injury and scarring around the nerve roots. However, there is room for improvement over current TLIF implants, instruments, and/or surgical procedures, such as the need to accurately place a TLIF implant into a vertebral space.

In view of the above, it is an object of the present invention to provide an improved TLIF implant, an instrument for implanting the improved TLIF, and a surgical procedure for the implantation. It is another object of the present invention to provide a steerable TLIF implant and implantation instrument therefor. It is still further an object of the present invention to provide a spine implant for vertebral fusion that is positionable within an interbody space via an associated implantation instrument. Other objects are contemplated.

SUMMARY

An implant, instrument, and procedure is provided for vertebral fusion such as, but not limited to, a transforaminal lumbar interbody fusion (TLIF).

The spine implant is designed to be steered or guided into place during implantation into a vertebral space by a complementary insertion or implantation instrument through the ability of the spine implant to rotate relative to the insertion instrument and the insertion instrument to control rotation of the spine implant. The spine implant is constrained to a limited range of rotation about a cylindrical pivot post retained in the implant. The insertion instrument is structured to engage the pivot post and controllably rotate the implant relative to the post in order to angularly position the implant during insertion. Range of rotational motion is controlled by a radial groove in the outside surface of the pivot post and a retaining pin that extends from a bore in the sidewall of the implant and is received into the groove thereby rotationally connecting the implant to the pivot post. Cutouts formed at upper and lower overhangs at the opening to the pivot post of the implant provide rotational stability to the implant during installation. A distal protrusion on the insertion instrument provides a keyed feature that interfaces with the implant to aid in maintaining a connection between the insertion instrument and the implant throughout implantation.

One longitudinal end of the implant is configured for transforaminal reception of the implant while an opposite longitudinal end is configured for axial reception and retention of the pivot post and longitudinal reception of the insertion instrument by the pivot post. A bore in a lateral side of the implant provides communication by a pin retained in the lateral bore with the radial groove of the pivot post. The pivot post includes a threaded, blind hole in its side. An opening in the longitudinal end of the implant allows access to the threaded hole of the pivot post to allow a threaded rod of the insertion instrument to attach to the post. The arcuate opening is configured to allow the implant to pivot a given amount to one side relative to the pivot post when the pivot post is connected to the threaded rod of the insertion instrument. The arc length of the opening determines the amount of pivoting of the implant.

The longitudinal end supporting the pivot post has an upper ledge or shelf, and a lower ledge or shelf. The upper ledge has an axial opening sized to axially receive the pivot post. The lower ledge has a base configured to receive the bottom of the pivot post and allow rotation thereof. The upper and lower ledges define the longitudinal inserter instrument opening. The upper ledge has an arcuate cutout in its lower surface. The lower ledge has an arcuate cutout in its upper surface. The arcuate cutouts in the upper and lower surfaces receive a protrusion situated on a distal face of the distal end of the insertion instrument adjacent the threaded rod that aid in retaining, guiding and/or stabilizing the implant during rotational movement of the implant during implantation.

The implant is preferably, but not necessarily, porous. An opening preferably, but not necessarily, extends through the implant from an upper surface to a lower surface thereof.

In one form, the implant has a generally linear body. In another form, the implant has a curved body.

The insertion instrument is characterized by a handle supporting a frame that is attached to a hollow shaft. A rod having a threaded end extends through the hollow shaft and is connected to a first or upper knob/controller within the frame, the threaded end of the rod configured to be threadedly received in the threaded bore of the pivot post. Rotation of the first knob rotates the rod to thread (attach) or unthread (detach) the threaded end from the pivot post (i.e. controls attachment). The insertion instrument also has a second knob/controller attached to a flat movable push bar that is movably retained in a lateral side of the inserter body, the flat movable push bar actuated (moved) by the second or lower knob. Actuation or longitudinal movement of the lower knob translates the flat movable push bar to change the angular position of (angulate) the attached implant through rotation of the implant about the pivot post. A second lateral bar is situated on the other lateral side of the inserter body and is stationary to help retain the implant along with a protrusion situated on a distal face of the distal end of the insertion instrument adjacent the stationary second lateral bar.

In another form, the insertion instrument has two push bars retained in the inserter body via dove-tailed articulation that is actuated by the second or lower handle/knob. Actuation (rotation) of the lower know translates the two push bars to change the angular position of (angulate) the attached cage through rotation of the cage about the pivot post.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate the present invention, wherein:

FIG. 10 is a sectional view of the steerable TLIF spine implant of FIG. 9;

FIG. 11 is an isometric view of the steerable TLIF spine implant of FIG. 8 with an end thereof in sectional;

FIG. 12 is an enlarged isometric view of a pivot post of the steerable TLIF spine implant of FIG. 8;

DETAILED DESCRIPTION

Figure 1:
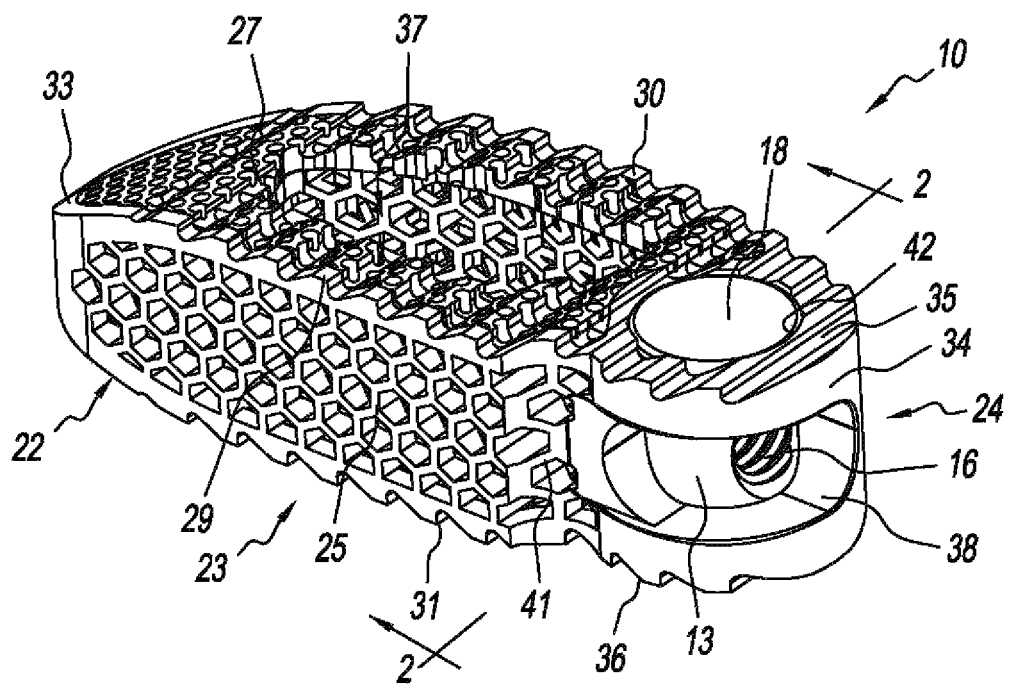
FIG. 1 is an isometric view of a steerable TLIF spine implant fashioned in accordance with the present principles.
Figure 2:
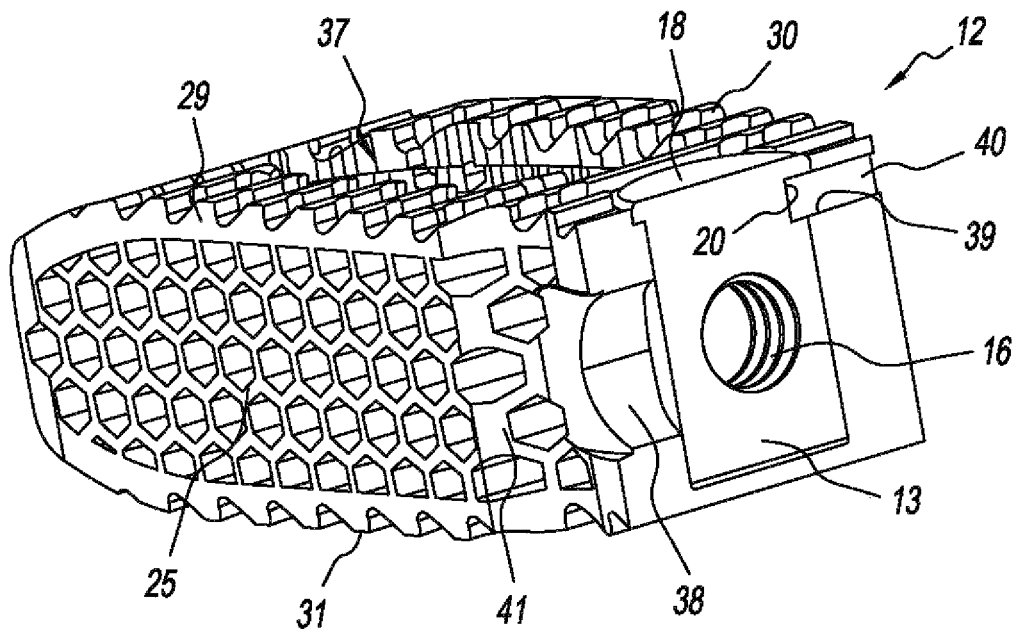
FIG. 2 is an isometric view of the steerable TLIF spine implant of FIG. 1 with a portion thereof in sectional.
Figure 3:
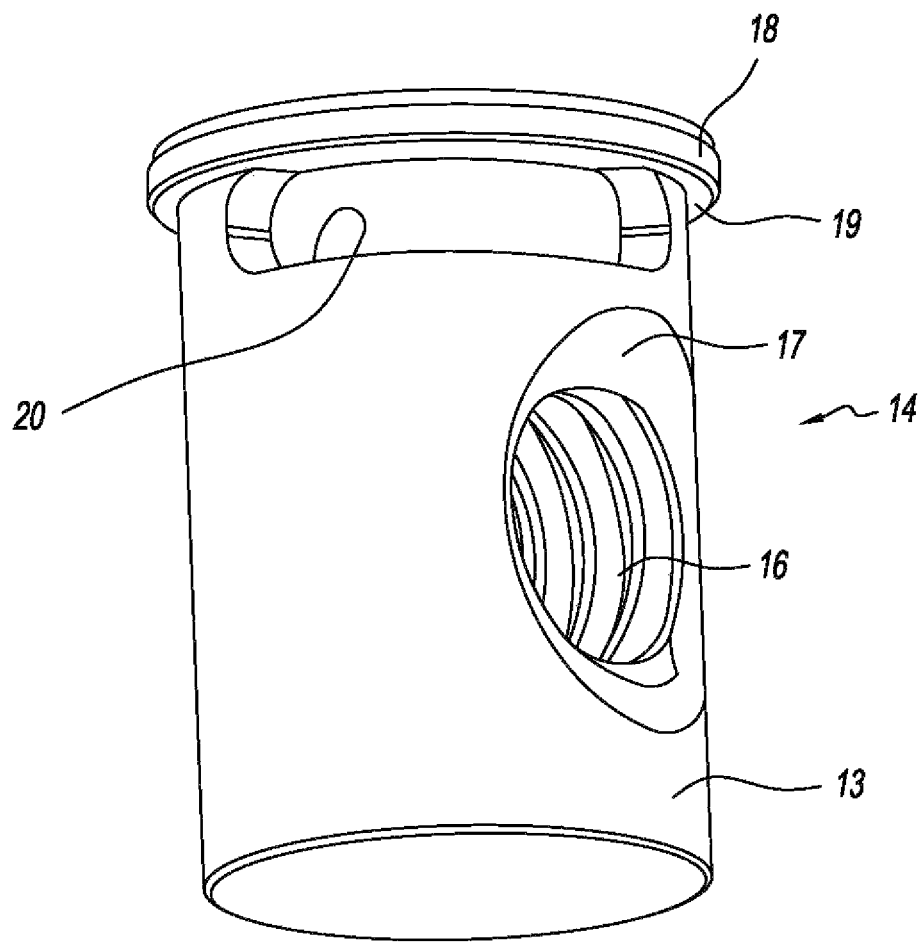
FIG. 3 is an enlarged isometric view of a pivot post of the steerable TLIF spine implant of FIG. 1.

Referring to FIGS. 1-3, there is depicted an exemplary form of a transforaminal lumbar interbody fusion (TLIF) implant (spine implant), generally designated 10, fashioned in accordance with the present principles, that is able to be steered or guided into a vertebral space via an installation instrument. The TLIF implant 10 is made from a biocompatible material such as, but not limited to, titanium, stainless steel, an alloy of titanium or stainless steel, PEEK, solid PEEK, other plastics and polymers, and otherwise. The TLIF implant 10 is characterized by a cage or interbody device 12 and a post 14. The post 14 is preferably, but not necessarily, removable from and insertable into the cage 12 and allows the cage 12 to rotate relative to the post 14.

The post 14 is particularly shown in FIG. 3. The post 14 has a generally cylindrical body 13 with a head 18 on one end defining an under surface 19. As seen in FIG. 2, the under surface 19 is retained by a ledge of a bore of the cage 12. The post 14 also has a threaded hole 16 in its outer surface preferably, but not necessarily having a tapered region 17 surrounding the threaded hole 16. The tapered region 17 aids in receiving a threaded rod 53 of an insertion instrument 50. The post 13 further has a radial slot 20 in its outer surface that is preferably, but not necessarily, adjacent the under surface 19 of the head. The radial slot 20 has a length that determines the amount of rotation of the cage 12 about and relative to the post 13 as described herein. Changing the length of the slot 20 changes the amount of cage rotation/angulation. The longer the length, the greater the amount of rotation/angulation. The shorter the length, the lesser the amount of rotation/angulation. To this end, the cage 12 has a bore 39 that extends from the outer surface of the cage 12 to a large bore 42 of the head 34 of the cage 12. A retaining pin 40 is received in the bore 39 that extends into the large bore 42 of the head 34 and into the radial slot 20, thus rotationally constraining the rotation between the post 14 and the cage 12 to the arcuate length of the slot 20. The retaining pin 40 also axially retains the post 14 in the bore 42.

Referring back to FIGS. 1 and 2, the cage 12 is defined by a body 22 having a porous portion 23 that is shaped generally as a rectangle, and a head 24. The porous portion 23 is characterized by a generally sloped nose 33, an upper side 27, a lower side 28, a first lateral side 25, a second lateral side 26, a front or head 34, and a central cavity 37. The upper side 27 has a plurality of serrations, teeth or the like 35 along its length. The lower side 28 likewise has a plurality of serrations, teeth or the like 36 along its length. The serrations 35, 36 are angled to allow easy insertion of the cage 12 into a vertebral space (not shown), but inhibit its egress from the vertebral space (not shown).

The head 34 is generally round having an upper serrated surface 35 and a lower serrated surface 36. A large bore 42 is provided in the head 34 that extends from the upper serrated surface 35 to the lower serrated surface 36 and is sized to receive the post 14. The post 14 is rotatable in the bore 42 and thus relative to the cage 12. The cage 12 is rotatable relative to the post 14 when the post 14 is retained relative to the cage 12. The head 34 has a radial slot 38 in a front surface that is sized to allow access to the threaded bore 16 of the post 14. Changing the length of the slot 38 changes the amount of cage rotation and this angulation relative to the post 14. The longer the length, the greater the amount of rotation/angulation. The shorter the length, the lesser the amount of rotation/angulation. A notch 41 is provided at a lateral side of the head 34 that is configured to receive a pusher of the installation instrument.

Figure 4:
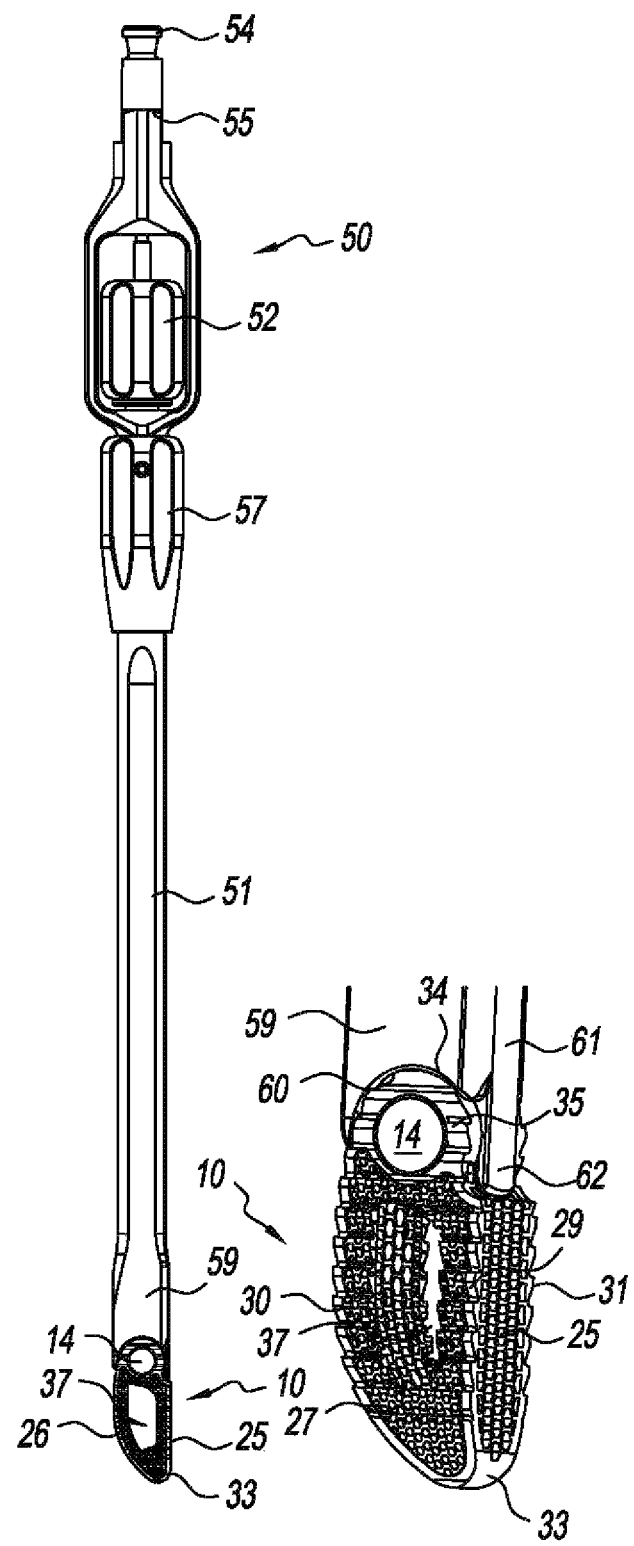
FIG. 4 is a combined illustration of a plan view of an inserter instrument for and attached to the steerable TLIF spine implant of FIG. 1, along with an enlarged isometric view of the steerable TLIF spine implant connected to the end of the inserter instrument, the steerable TLIF spine implant in an initial angular position and rotationally locked to the inserter instrument.
Figure 5:
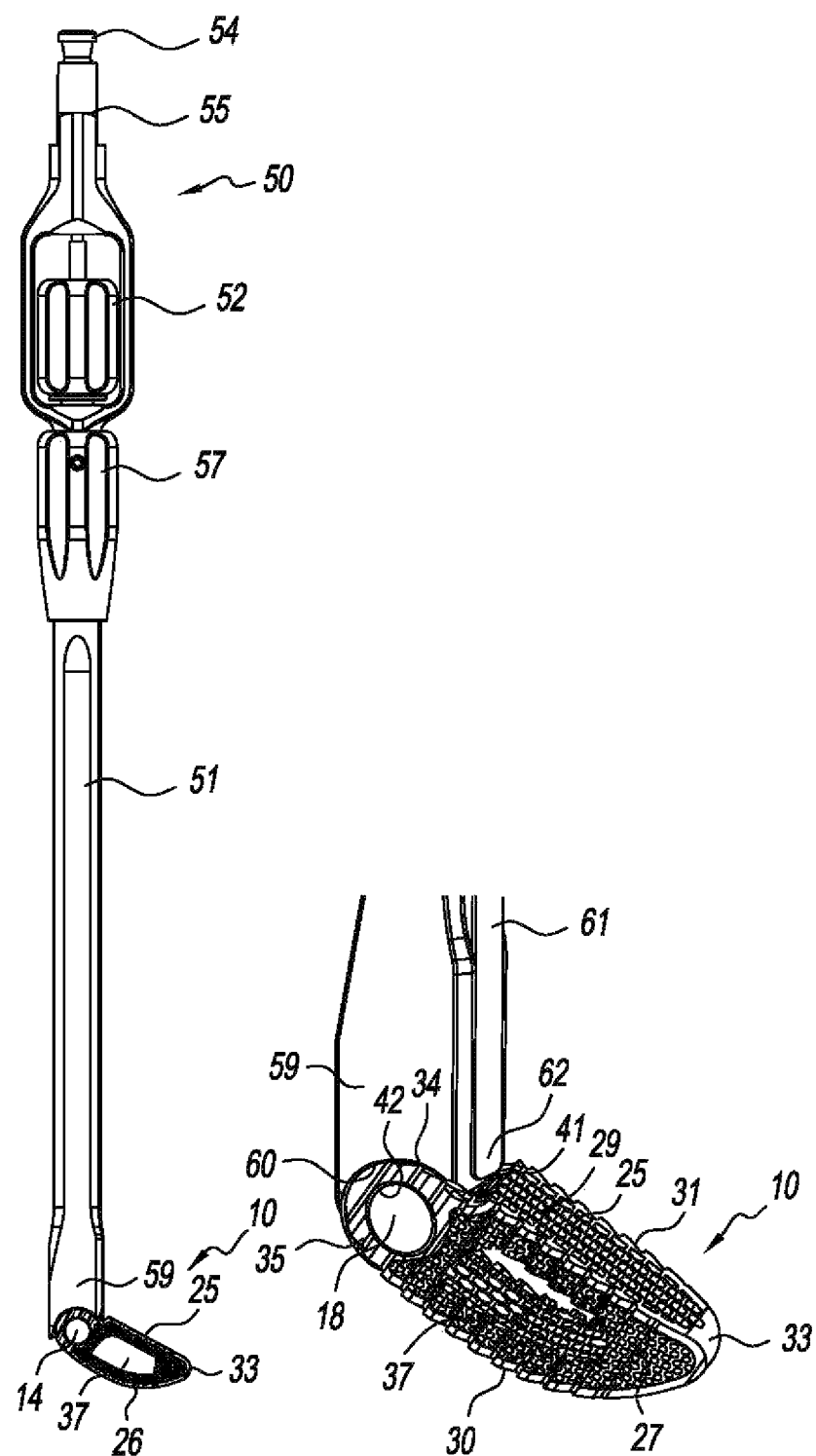
FIG. 5 is a combined illustration of a plan view of the inserter instrument for the steerable TLIF spine implant of FIG. 1, along with an enlarged isometric view of the steerable TLIF spine implant connected to the end of the inserter instrument, the steerable TLIF spine implant in a final angular position and rotationally unlocked from the inserter instrument.

Referring to FIG. 4 there is shown an installation instrument 50 for inserting the spine implant 10 within a vertebral space and angularly positioning/orientating the spine implant 10 into and/or within the vertebral space. In FIG. 4, the spine implant 10 is in an initial angular position and rotationally locked to an inserter/inserter portion 59 of the installation instrument 50. FIG. 5 shows the installation instrument 50 and the spine implant 10 in a final angular position and rotationally unlocked from the inserter 59 of the installation instrument 50.

Figure 6:
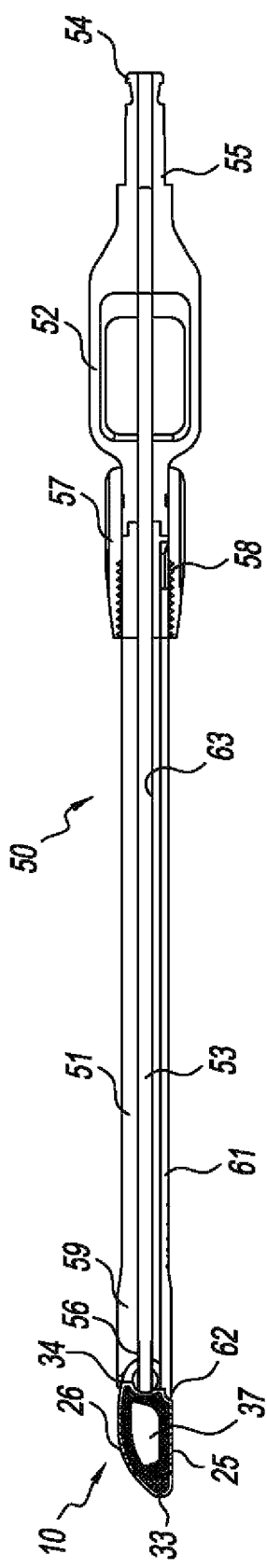
FIG. 6 is a sectional view of the inserter instrument of FIGS. 4 and 5 shown attached to the steerable TLIF spine implant of FIG. 1.
Figure 7:
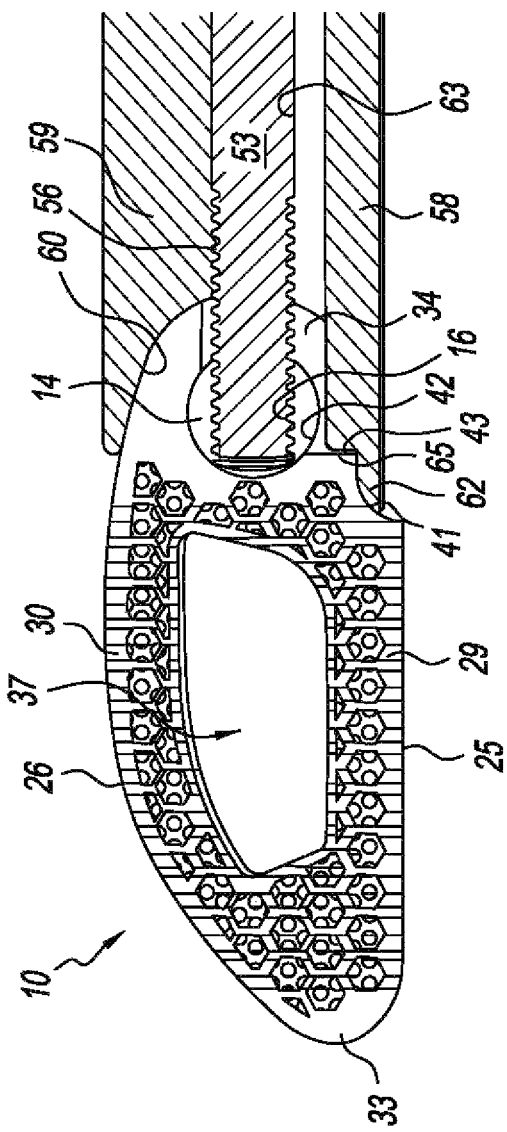
FIG. 7 is an enlarged sectional view of the end of the inserter instrument connected to the steerable TLIF spine implant of FIG. 1.

FIG. 6 shows the installation instrument 50 in sectional, while FIG. 7 shows a close-up the end of the installation instrument connected to the spine implant 10, both in sectional. A curved end portion 60 receives the curved head 34 of the implant 10. The installation instrument 50 has a shaft 51 that is connected to an upper handle 52 and having a longitudinal bore 63. A rod 53 extends through the bore 63 of the shaft 51 and has a knob 54 at a distal end 55, and threads at another end 56, the rod 53 axially movable relative to the shaft through rotation of the knob 54. In this manner the threaded end 56 of the rod 53 can be threaded into the threaded hole 16 of the post 14 (as shown in FIG. 7) by rotation in a first direction, or be unthreaded from the threaded hole 16 of the post 14.

Figure 8:
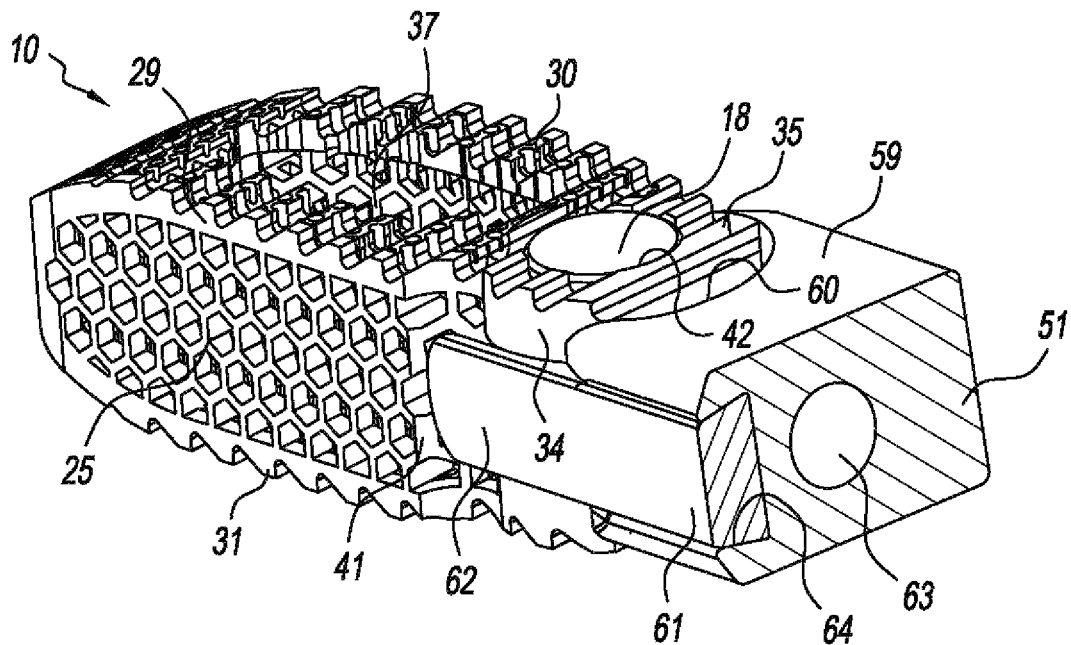
FIG. 8 is an isometric view of another steerable TLIF spine implant attached to an end of another inserter instrument with the end of the inserter instrument in sectional.
Figure 9:
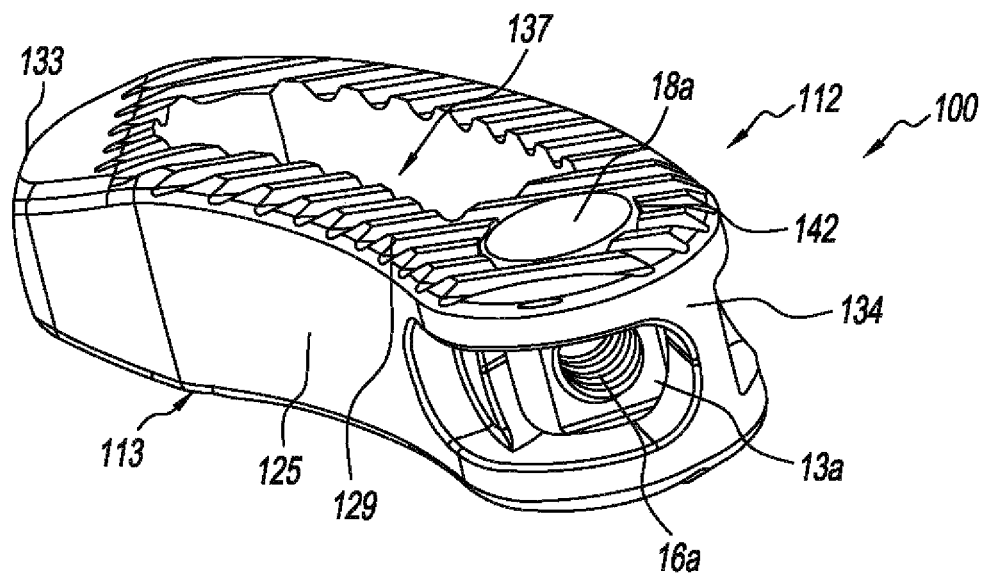
FIG. 9 is an isometric view of the steerable TLIF spine implant of FIG. 8.

As depicted in FIGS. 7 and 8, the installation instrument 50 also has a pusher 61 that extends along the outside of the shaft 51 in a channel 64. The pusher 61 and the channel 63 are preferably, but not necessarily, of a dove-tail configuration. Other configurations may be used. The pusher 61 has a flanged end 62 that is received in the notch 41 of the implant 10. A shoulder 65 of the end contacts a ledge 42 of the notch 41. The pusher 61 is attached to the lower handle 57 such that rotation of the lower handle 57 axially moves the pusher 61. Inner threads 58 of the lower handle 57 interact with upper external threads of the shaft 51 to effect axial/longitudinal movement of the pusher 61 to lock and unlock rotation of the cage 10.

FIGS. 9-12 illustrate another form of a TLIF implant, generally designated 100, fashioned in accordance with the present principles. The TLIF spine implant 100 is characterized by a cage or interbody device 112 and a post 14a. The post 14a is preferably, but not necessarily, removable from and insertable into the cage 112 and allows the cage 112 to rotate relative to the post 14a.

The post 14a is particularly shown in FIG. 12. The post 14a has a generally cylindrical body 13a with a planar head 18a on one end. The post 14a also has a threaded hole 16a in its outer surface preferably. The post 14a further has a radial slot 20a in its outer surface that is preferably, but not necessarily, adjacent the head 18a. The radial slot 20a has a length that determines the amount of rotation of the cage 112 about and relative to the post 14a as described herein. Changing the length of the slot 20a changes the amount of cage rotation/angulation. The longer the length, the greater the amount of rotation/angulation. The shorter the length, the lesser the amount of rotation/angulation. To this end, the cage 112 has a bore that extends from the outer surface of the cage 112 to a large bore 142 of the head 134 of the cage 112. A retaining pin 40 is received in the bore that extends into the large bore 142 of the head 134 and into the radial slot 20a, thus rotationally constraining the rotation between the post 14a and the cage 112 to the arcuate length of the slot 20a. The retaining pin 40 also axially retains the post 114 in the bore 142.

The cage 112 is defined by a body 113 that is shaped generally as an arch with a head 134. The body 113 is characterized by a generally sloped nose 133, a serrated upper side 129, a serrated lower side (not seen), a curved first lateral side 125, a curved second lateral side 126, a front or head 134, and a central cavity 137. The serrations of the upper and lower sides are angled to allow easy insertion of the cage 112 into a vertebral space (not shown), but inhibit its egress from the vertebral space (not shown).

The head 134 is generally round having an upper serrated surface and a lower serrated surface. A large bore 142 is provided in the head 134 that extends from the upper serrated surface to the lower serrated surface and is sized to receive the post 14a. The post 14a is rotatable in the bore 142 and thus relative to the cage 112. The cage 112 is rotatable relative to the post 14a when the post 14a is retained relative to the cage 112. The head 134 has a radial slot 144 in a front surface that is sized to allow access to the threaded bore 16a of the post 14a. Changing the length of the slot changes the amount of cage rotation and thus angulation relative to the post 14a. The longer the length, the greater the amount of rotation/angulation. The shorter the length, the lesser the amount of rotation/angulation. A notch 145 is provided at a lateral side of the head 134 that is configured to receive a pusher of the installation instrument.

Figure 13:
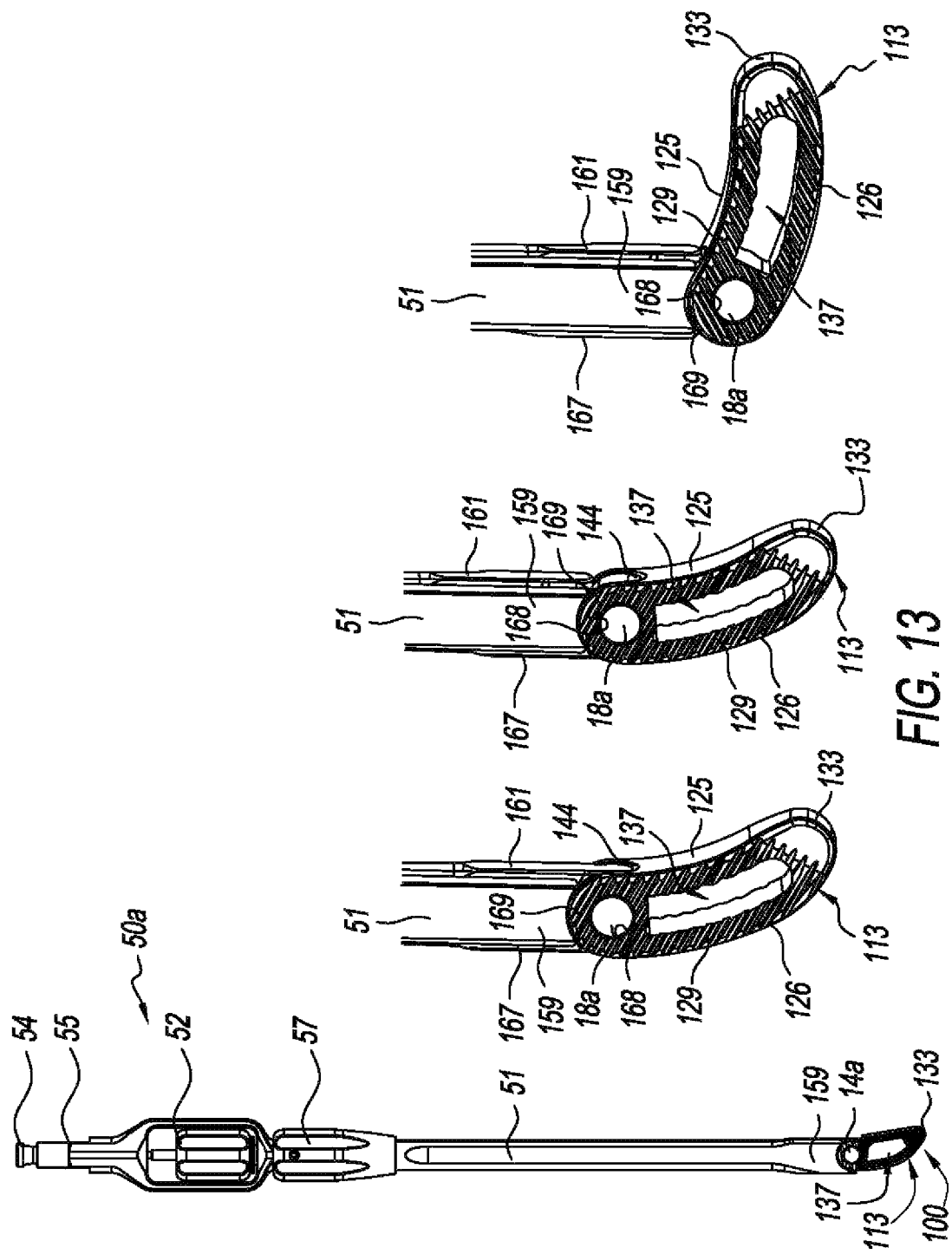
FIG. 13 is a combined illustration of the inserter instrument for and attached to the steerable TLIF spine implant of FIG. 8, along with a sequence of three enlarged views of the steerable TLIF spine implant of FIG. 8 on the end of the inserter instrument illustrating angular positioning of the steerable TLIF spine implant.

FIG. 13 provides a sequence of drawings illustrating the angulation ("steerability") of the TLIF spine implant 100 through implantation via an insertion instrument 50a, from an initial angular position through a final angular position. The insertion instrument 50a has the same features and components as the insertion instrument 50 but its inserter 159 includes first and second lateral pushers 161, 167. A curved end 169 of the inserter 159 mates with the end 168 of the implant 100, while the first and second lateral pushers 161, 167 are received in the lateral slots of the implant 100 to provide controlled angulation (angular positioning) of the implant 100. The implant 100 is received by the insertion instrument 50a through its threaded rod received in the threaded bore of the post 14a in like manner as the other TLIF spine implants discussed herein.

Figure 14:
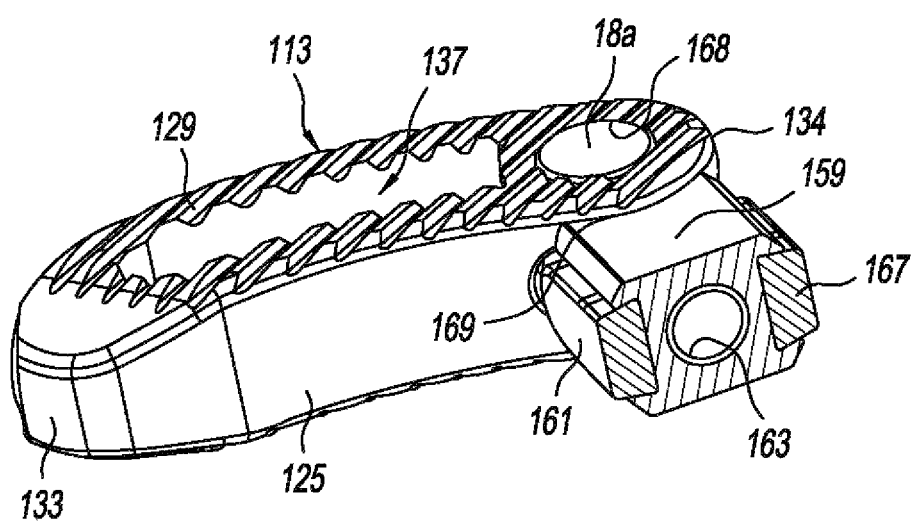
FIG. 14 is an isometric view of the steerable TLIF spine implant of FIG. 8 attached to an end of another inserter instrument, the end in sectional.
Figure 15:
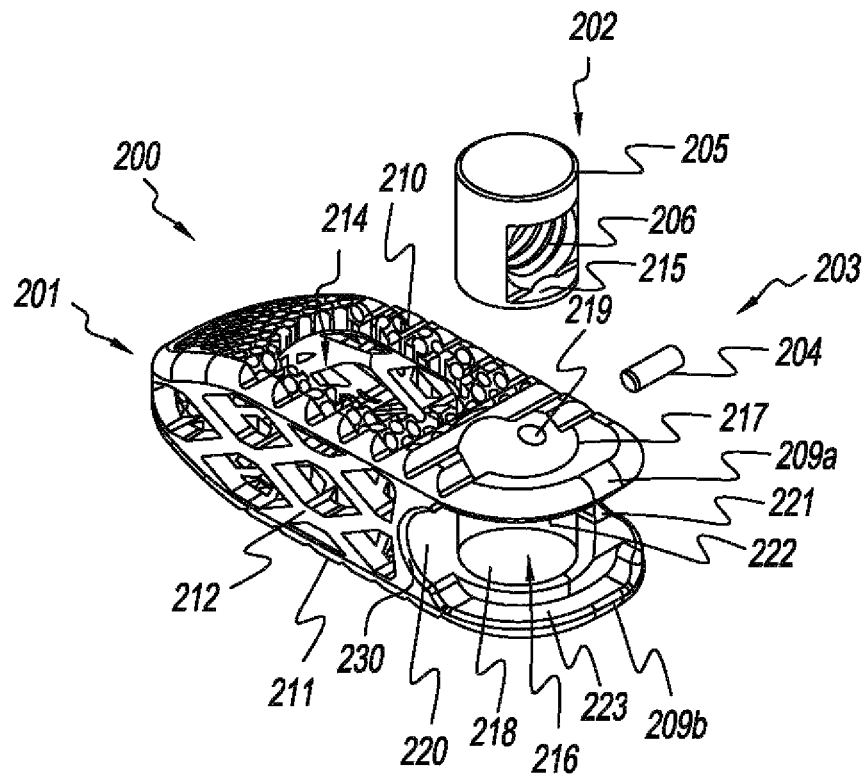
FIG. 15 is an exploded isometric view of another steerable TLIF spine implant.
Figure 16:
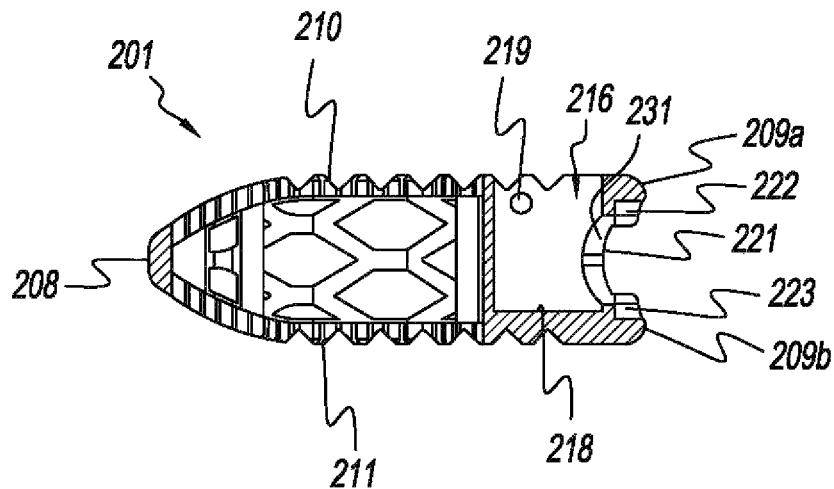
FIG. 16 is a side sectional view of the cage of the steerable TLIF spine implant of FIG. 15.

FIG. 14 shows the TLIF spine implant of FIGS. 9-13 with another version of an inserter 159 of an insertion instrument. The inserter 159 includes two (2) push rods 161, 167 that are retained in the inserter body via dove-tail axial translation and actuated by turning (rotating) the lower knob of the insertion instrument.

Referring to FIGS. 15-21, there is depicted another exemplary form of a transforaminal lumbar interbody fusion (TLIF) implant (spine implant or implant), generally designated 200, fashioned in accordance with the present principles, that is able to be steered or guided into a vertebral space via an inserter, installation or implantation instrument 300 (see FIGS. 22-28). It should be appreciated however, that the implant 200 may be used as a spine implant for places other than the lumbar region and for purposes other than transforaminal. The present spine implant 200, however, will hereinafter be discussed as a TLIF implant 200. The TLIF implant 200 is made from a biocompatible material such as, but not limited to, titanium, stainless steel, an alloy of titanium or stainless steel, PEEK, solid PEEK, other plastics and polymers, and otherwise. The TLIF implant 200 is characterized by a cage 201, a pivot post 202, and a retaining pin 203. The pivot post 202 is preferably, but not necessarily, removable from and insertable into the cage 201 and allows the cage 201 to rotate relative to the pivot post 202.

Figure 17:
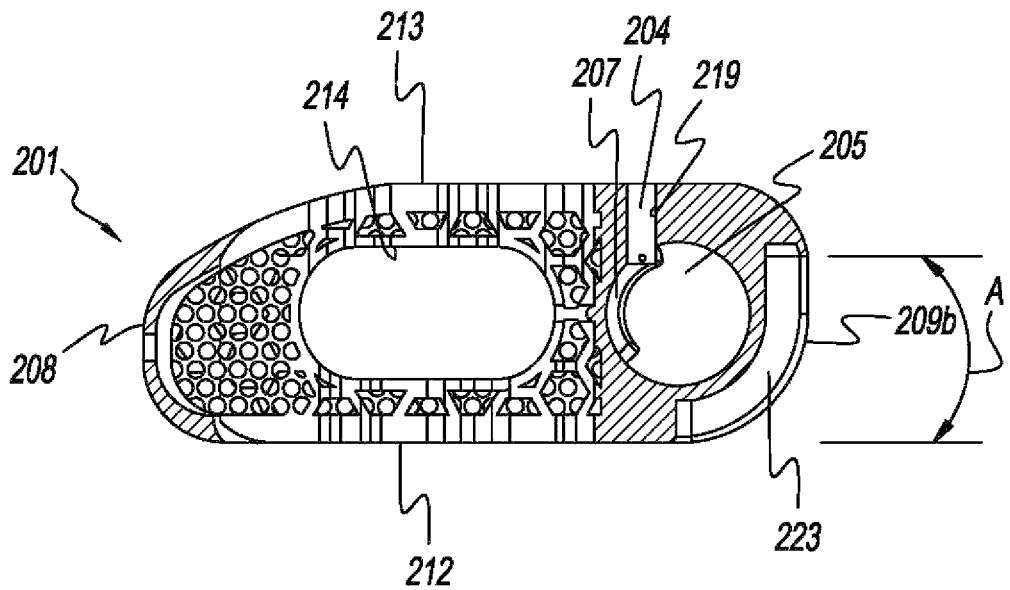
FIG. 17 is a top sectional view of the cage of the steerable TLIF spine implant of FIG. 15.
Figure 18:
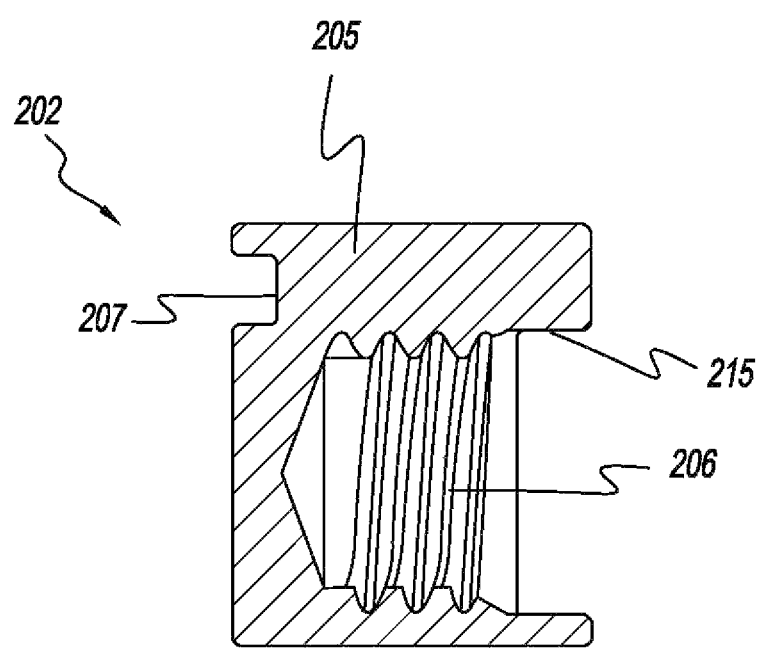
FIG. 18 is an enlarged sectional view of a pivot post of the steerable TLIF spine implant of FIG. 15.
Figure 19:
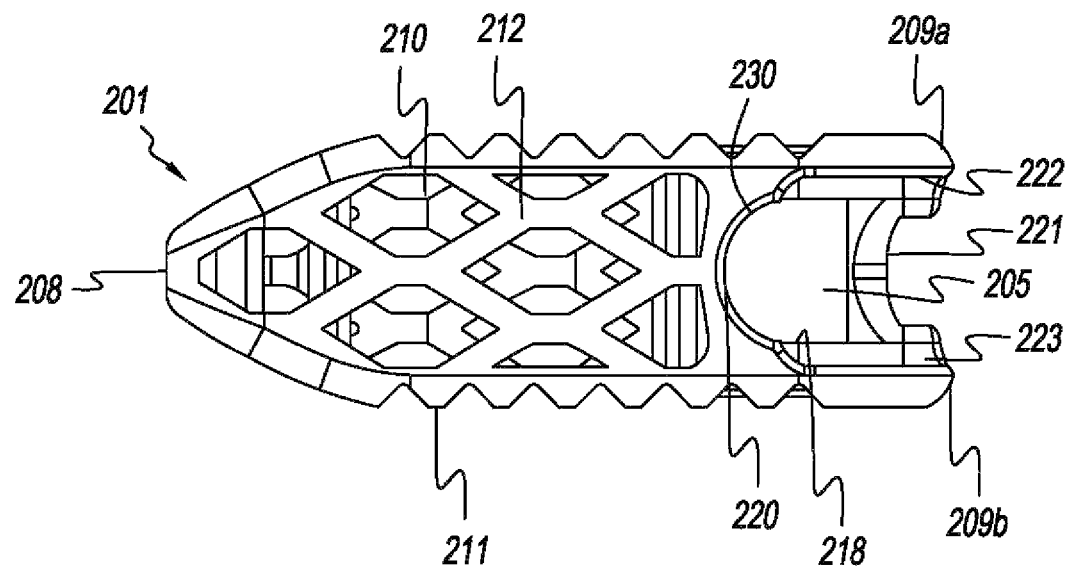
FIG. 19 is an enlarged side sectional view of the cage of the steerable TLIF spine implant of FIG. 15.
Figure 20:
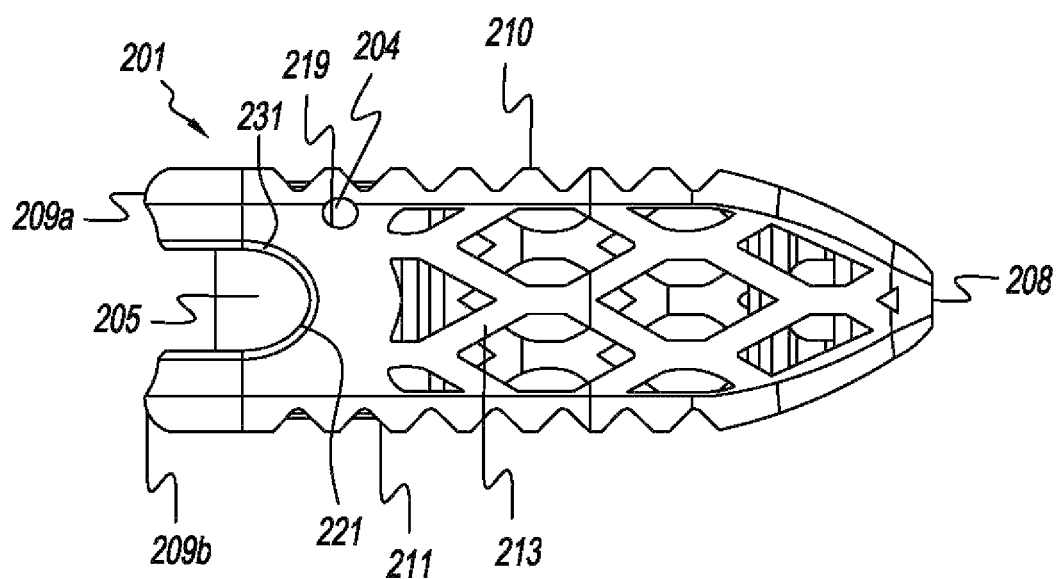
FIG. 20 is an enlarged side sectional view of the cage of the steerable TLIF spine implant of FIG. 15, opposite to the view of FIG. 19.
Figure 21:
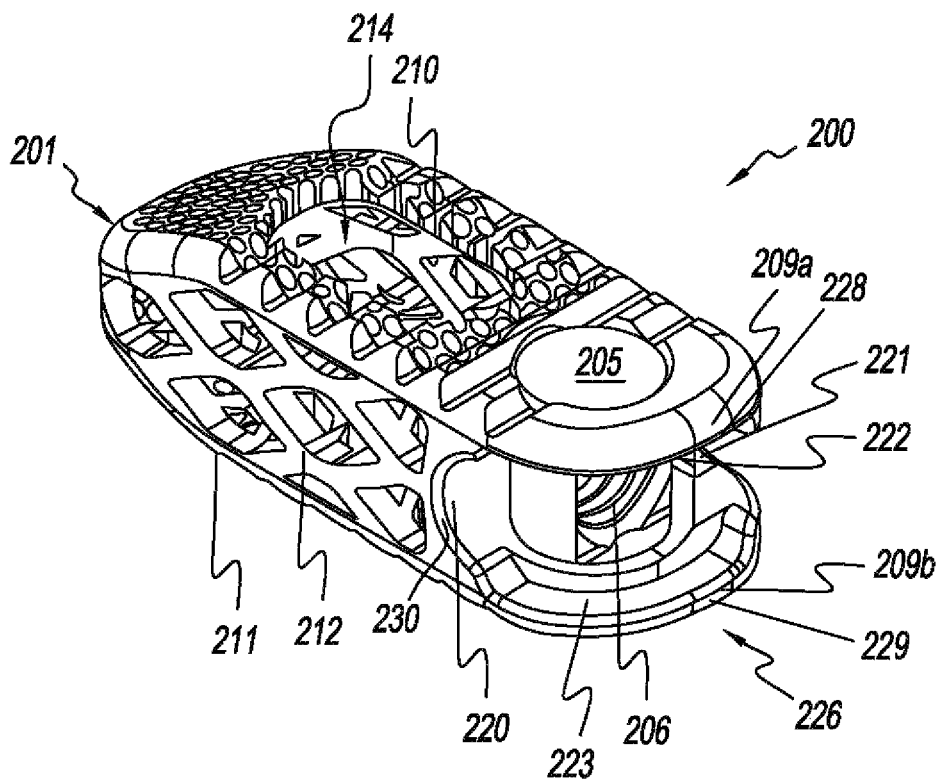
FIG. 21 is an isometric view of the steerable TLIF spine implant of FIG. 15.
Figure 22:
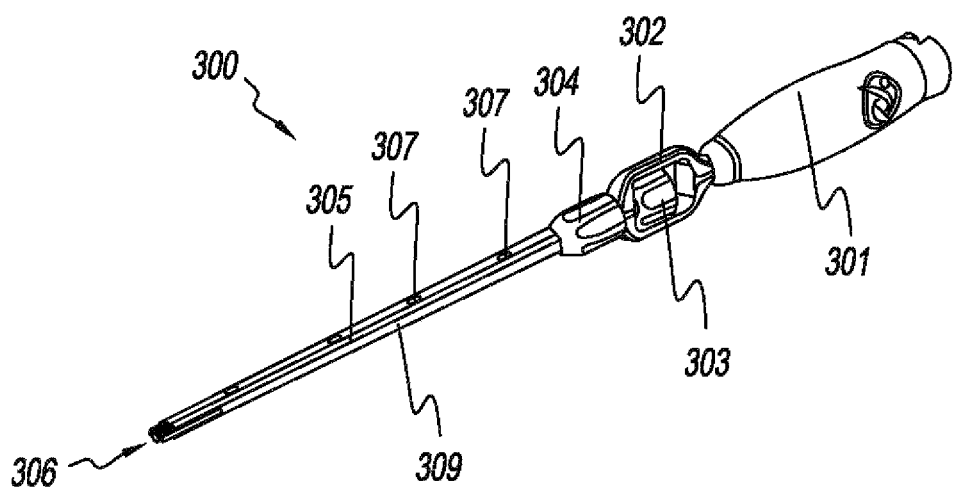
FIG. 22 is an isometric view of an installer or implantation instrument for the steerable TLIF spine implant of FIG. 15.

The retaining pin 203 is defined by an elongated cylindrical body, cylinder or rod 204 and is sized for reception in a lateral bore 219 of the cage 201 as explained more fully below. With particular reference to FIGS. 17 and 18, the pivot post 202 is defined by a cylinder or cylindrical body 205. A cutout 215 is formed in the circumferential side of the cylinder 205 with a threaded bore 206 extending radially inward toward a longitudinal axis of the cylinder 205. The cutout 215 and the threaded bore 206 are not preferably, but not necessarily, centered between the upper and lower surfaces of the pivot post, but are slightly more towards the lower surface than the upper surface. A radial channel or groove 207 is formed in the outside, outer or exterior circumferential surface of the cylinder 205. The radial channel 207 extends an arcuate distance radially along the circumferential surface of the cylinder 205. The radial channel 27 is axially above the cutout 215 and the threaded bore 206.

The cage 201 is formed as a generally porous body and as a generally elongate ovoid with a slight curve along its longitudinal length. Other shapes may be used. The cage 201 has an upper surface 210 that is preferably, but not necessarily, porous and/or mesh-like with serrations or ridges as seen in the figures, the pattern, configuration and style of porosity/mesh is also preferable, but not necessarily so. The cage 201 has a lower surface 211 that is preferably, but not necessarily, porous and/or mesh-like with serrations or ridges as seen in the figures, the pattern, configuration and style of porosity/mesh is also preferable, but not necessarily so. A first lateral side 212 extends between the upper surface 210 and the lower surface 211. The first lateral side 212 is also porous via a lattice structure, however, other structures may be used. A second lateral 213 extends between the upper surface 210 and the lower surface 211. The second lateral side 213 is also porous via a lattice structure, however, other structures may be used. As used herein and throughout, the nomenclature first and second, and upper and lower is arbitrary unless specified otherwise. Preferably, but not necessarily, the cage 201 has a medial, central, middle, or centrally located cavity 214 that extends from the upper surface 210 to the lower surface 211. The cavity 214 may hold bone graft material.

The cage 201 defines a first end 208 that is shaped generally as a bullet and may be termed a nose. A second end 209 formed as an upper shelf or ledge 209a and a lower shelf or ledge 209b is defined longitudinally opposite the first end 208 as well as an opening 226. The opening 226 has a first concave side wall 220 extending from the upper shelf 209a to the lower shelf 209b at the first lateral side 212, and a second concave side wall 221 opposite the first concave side wall 220 and extending from the upper shelf 209a to the lower shelf 209b at the second lateral side 213. The second concave side wall 221 extends longitudinally further towards the end edges 228, 229 of the upper and lower shelves 209a, 209b than the first concave side wall 220 to create an arcuate opening 226. As shown in FIG. 17, the opening 226 has an arcuate length A, which corresponds to the amount of pivot of the cage 201 about the pivot post 205. A first concave groove or channel 230 is formed about the first concave side wall 220 for receiving a movable bar 309 of the insertion instrument 300, the first concave groove 230 aiding in stabilizing the insertion instrument 300 onto the cage 201, and vice versa, as well as the implant process. Likewise, the second concave groove or channel 231 is formed about the second concave side wall 221 for receiving a stationary bar 310 of the insertion instrument 300, the first concave groove 230 aiding in stabilizing the insertion instrument 300 onto the cage 201, and vice versa, as well as the implant process.

A round bore 217 is formed adjacent the opening 226 from the upper surface 210 proximate the upper shelf 209a and extends to a pivot seat 218 to form a pivot post cavity 216 sized to rotatably receive the pivot post 205. A cylindrical bore 219 extends from an upper area of the second lateral side 213 proximate the edge 228 of the upper shelf 209a and into the pivot post cavity 216. The cylindrical pin 204 is received in the cylindrical bore 219 and extends into the radial channel 207 of the pivot post 205. The arcuate length of the radial channel 207 defines an amount or length of pivoting of the cage 201 relative to the pivot post 205. The cylindrical pin 204 thus limits rotational pivoting. Additionally, a lower arcuate channel or groove 223 is formed in the upper surface of the lower shelf 209b while a corresponding and axially coinciding upper arcuate channel or groove 222 is formed in a lower surface of the upper shelf 209a. The lower and upper arcuate channels 223, 222 define an arcuate length, path or guide that receives a distal projection 311 of the insertion instrument 300. This aids in stabilization and pivoting of the implant 200 relative to the insertion instrument 300 and vice versa.

Referring to FIGS. 22-28, there is shown an inserter, insertion or implantation instrument 300 for the TLIF spine implant 200 by itself and in conjunction with the implant 200. The insertion instrument 300 has a handle 301 having a proximal end and a distal end. A frame 302 housing a first rotatable knob or controller 303 and having a proximal end and a distal end, is connected at its proximal end to the distal end of the handle 301. The distal end of the frame 302 is connected to a second knob/controller 304. A hollow shaft 305 extends from the second rotatable knob or controller 304. A rod 312 has a proximal end (not seen) operably connected to the first rotatable knob 303 and extends through the hollow shaft 305. The distal end 306 of the rod 312 has a neck 311 and terminates in a threaded end 314. The threaded end 314 is sized and configured for threaded engagement with the threaded bore 206 of the pivot post 205. Rotation of the first rotatable know 303 rotates the rod 312 to thread and unthread the threaded end 314 into and out of the threaded bore 203 of the pivot post 205 to engage and disengage the implant 200.

Figure 23:
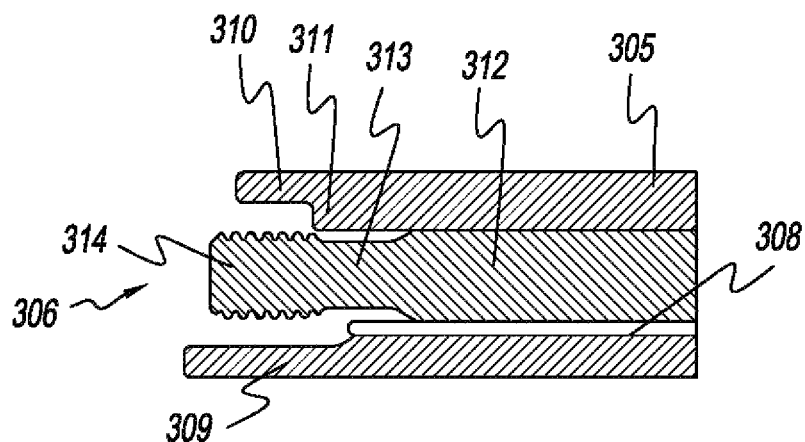
FIG. 23 is an enlarged sectional view of a distal end portion of the implantation instrument of FIG. 22.
Figure 24:
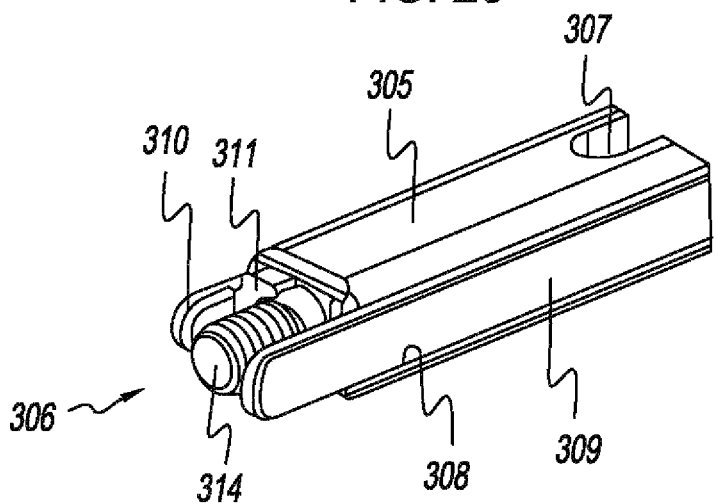
FIG. 24 is an enlarged isometric view of the distal end portion of the implantation instrument of FIG. 22 with a movable installation tang thereof in an extended position.
Figure 25:
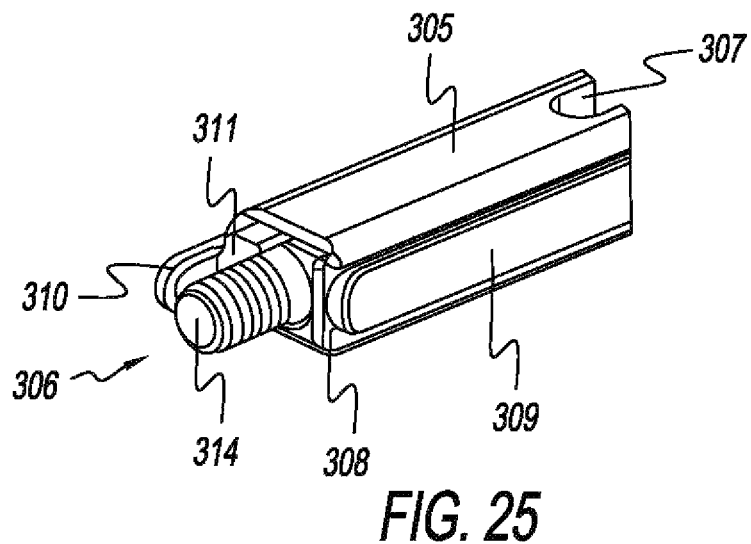
FIG. 25 is an enlarged isometric view of the distal end portion of the implantation instrument of FIG. 22 with the movable installation tang thereof in a retracted position.

The hollow shaft 305 has a series of ports 307 along its longitudinal length. The hollow shaft 305 has a longitudinal groove 308 along a first lateral side that retains an elongated rail 309 such that the elongated rail 309 is longitudinally movable in the longitudinal groove 308. The elongated rail 309 is connected at its proximal end to the second controller/knob 304. The second controller 304 is longitudinally movable or translatable on and along the hollow shaft 305. The movable bar 309 is disposed in a lateral channel 308 in a lateral side of the hollow shaft 305 such that the movable bar 309 is longitudinally movable or translatable in the channel 308. The proximal end of the movable bar 309 is connected to the second controller/knob 303 such that translation of the controller 303 translates the movable bar 309. As seen in FIGS. 23-25 position of the movable bar 309 and thus the end 316 (see FIG. 28) positions the end 316 beyond, at, or behind the threaded shaft 314 and a fixed bar 310 on the lateral side of the hollow shaft 305 opposite the movable bar 309. The fixed bar 310 engages the concave groove 231 of the concave side 221. Translation of the movable bar 309 pivots the implant 200 about the pivot post 305 and thus relative to the insertion instrument 300 that is temporarily fixed to the pivot post 305.

Figure 26:
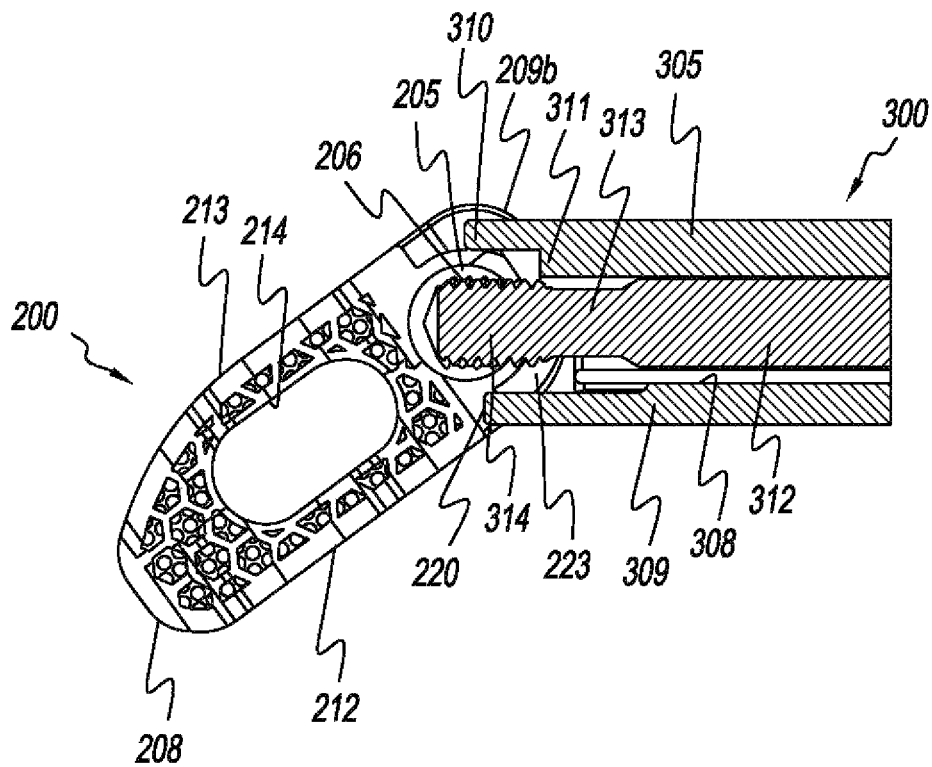
FIG. 26 is a top sectional view of the steerable TLIF spine implant of FIG. 15 attached to the implantation instrument of FIG. 22.
Figure 27:
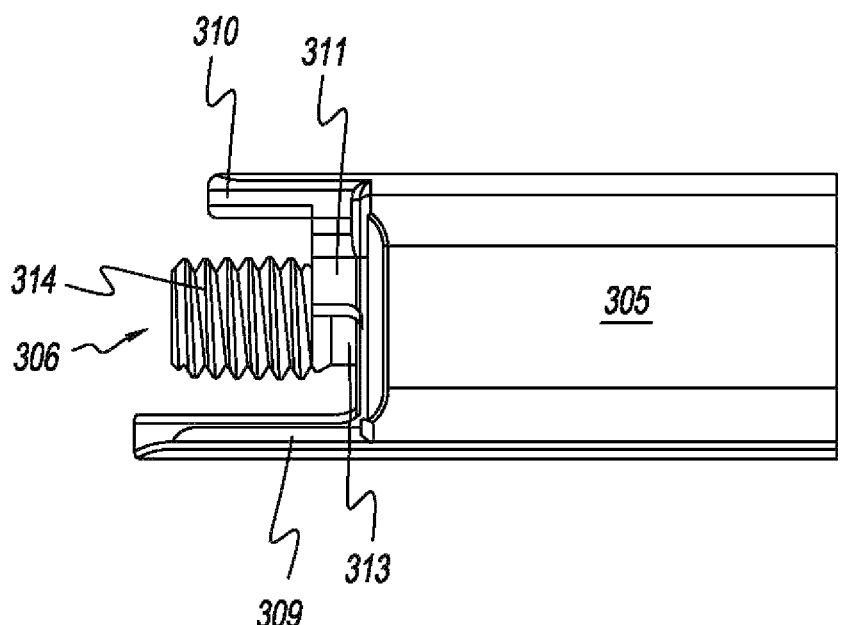
FIG. 27 is an enlarged isometric view of the distal end portion of the implantation instrument of FIG. 22 with the movable tang in an extended position.
Figure 28:
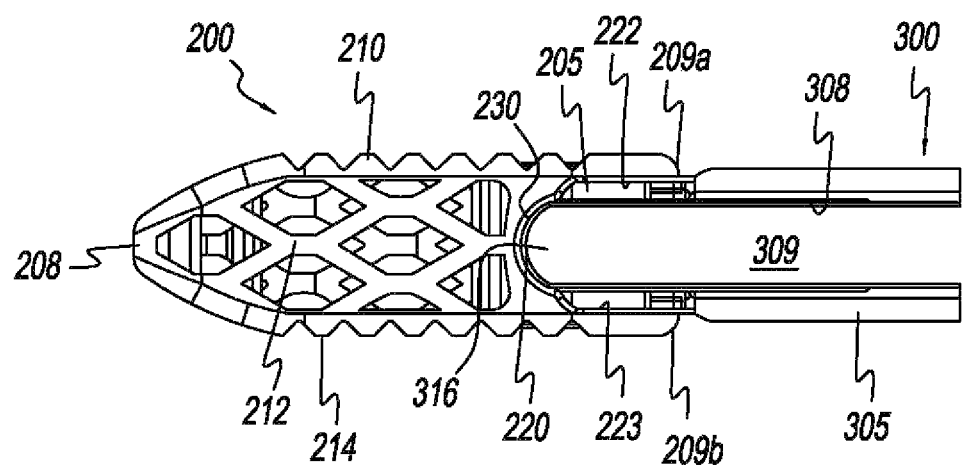
FIG. 28 is an enlarged side view of the steerable TLIF spine implant of FIG. 15 attached to the implantation instrument of FIG. 22.

Connection and rotational guiding or steering of the implant 200 and insertion instrument 300 are depicted in FIGS. 26 and 28. FIG. 28 illustrates via a side view how the convex end 316 of the movable bar 309 of the insertion instrument 300 engages the concave groove 230 and/or the concave side wall 220 of the implant 200.

A method of installation includes placing a TLIF spine implant 10/100/200 onto the insertion instrument 50/50a/300 and initially locking rotation of the implant relative to the post. During insertion of the implant, the rotation is unlocked and the pusher bar or rod(s) are used to angulate the implant as desired.

It should be appreciated that dimensions of the components, structures, and/or features of the present TLIF spine implants and insertion instruments may be altered as desired within the scope of the present disclosure.

What is claimed is:

1. An implant for a surgical procedure, the implant comprising:
   a cage having an upper side, a lower side opposite to the upper side, a first lateral side, a second lateral side opposite to the first lateral side, a first end, a second end opposite the first end, an arcuate opening in the second end defining an upper shelf extending longitudinally from the upper side and a lower shelf extending longitudinally from the lower side, the upper shelf having a first edge and a lower surface, the lower shelf having a second edge and an upper surface, a first bore in the upper side adjacent the upper shelf and extending axially from the upper side to the lower surface, a lower arcuate groove in the upper surface of the lower shelf adjacent the second edge, an upper arcuate groove in the lower surface of the upper shelf adjacent the first edge, the lower arcuate groove and the upper arcuate groove axially aligned with one another and forming an arcuate channel of a first arcuate length for receipt and guidance of a distal protrusion on a distal end of an implant installation instrument along the arcuate channel during pivotal movement of the cage during implantation of the implant, and a second bore in the second lateral side of the cage in communication with the first bore;
   a pivot post disposed in the first bore of the cage, the pivot post having a central axis and a third bore in a radial side thereof that extends inward; and
   a retention pin received in the second bore in the second lateral side of the cage and in contact with the pivot post to constrain the cage to a range of rotation about the post and along the arcuate channel.

2. The implant of claim 1, wherein the lower shelf further comprises a seat in the upper surface of the lower shelf and axially below the first bore, wherein the pivot post is rotationally supported on the seat.

3. The implant of claim 1, wherein the third bore is a threaded bore.

4. The implant of claim 1, wherein the pivot post further comprises a receptor disposed in an exterior surface of the pivot post.

5. The implant of claim 4, wherein the receptor is disposed opposite to the third bore.

6. The implant of claim 4, wherein:
   the receptor of the pivot post comprises a radial channel of a second arcuate length about the exterior surface; and
   the retention pin is in communication with the radial channel, wherein range of rotational movement of the cage relative to the pivot post is controlled by the second arcuate length of the radial channel of the pivot post.

7. The implant of claim 6, wherein the first arcuate length of the arcuate channel is equal to the second arcuate length of the radial channel.

8. The implant of claim 1, wherein the arcuate opening in the second end of the cage has a first concave wall on the first lateral side of the cage extending from the lower surface of the upper shelf to the upper surface of the lower shelf, and a second concave wall on the second lateral side of the cage extending from the lower surface of the upper shelf to the upper surface of the lower shelf.

9. The implant of claim 8, wherein the first concave wall is longitudinally offset from the first and second edges a first offset distance, and the second concave wall is longitudinally offset from the first and second edges a second offset distance, the second offset distance less than the first offset distance.

10. The implant of claim 9, further comprising:
a first arcuate wall groove in the first concave wall; and
a second arcuate wall groove in the second concave wall.

11. A kit for a surgical procedure, the kit comprising:
an implant comprising:
a cage having an upper side, a lower side opposite to the upper side, a first lateral side, a second lateral side opposite to the first lateral side, a first end, a second end opposite the first end, an opening in the second end defining an upper shelf extending longitudinally from the upper side and a lower shelf extending longitudinally from the lower side, the upper shelf having a first edge and a lower surface, the lower shelf having a second edge and an upper surface, a first bore in the upper side adjacent the upper shelf and extending axially from the upper side to the lower surface, a lower groove in the upper surface of the lower shelf adjacent the second edge, an upper groove in the lower surface of the upper shelf adjacent the first edge, the lower groove and the upper groove axially aligned with one another and forming a channel;
a pivot post disposed in the first bore of the cage, the pivot post having a central axis and a third bore in a radial side thereof that extends radially inward; and
a retention pin received in a second bore in the second lateral side of the cage and in contact with the pivot post to constrain the cage to a range of rotation about the post and along the channel; and
an installation instrument for the implant comprising:
a handle having a proximal end and a distal end;
a frame having a proximal end and a distal end, the proximal end of the frame attached to the distal end of the handle;
a hollow shaft having a proximal end and a distal end, the proximal end of the shaft attached to the distal end of the frame, the distal end of the hollow shaft is open;
a first controller longitudinally movably disposed on the proximal end of the hollow shaft;
a rod having a proximal end and a third distal end, the rod extending through the hollow shaft wherein the third distal end extends from the open distal end of the hollow shaft and is configured to engage and disengage the third bore of the pivot post;
a second controller attached to the distal end of the rod and retained in the frame, wherein rotation of the second controller rotates the rod to couple or detach the end of the rod from the pivot post;
a first bar having a proximal end and a distal end and movably retained in a first lateral side of the hollow shaft, the proximal end of the first bar attached to the first controller whereby longitudinal translation of the first controller longitudinally translates the first bar relative to the hollow shaft to move the first bar relative to the hollow shaft to extend and retract the distal end of the first bar to change the angular position of the attached cage through rotation of the cage about the pivot post;
a second bar disposed on and stationary relative to a second lateral side of the hollow shaft; and
a protrusion situated on a distal face of the distal end of the installation instrument adjacent the stationary second bar.

12. The kit of claim 11, wherein the channel defines a first arcuate length for receipt and guidance of a distal protrusion on a distal end of a spine implant installation instrument for a surgical procedure along the channel during pivotal movement of the cage during implantation of the implant, and the second bore in the second lateral side of the cage in communication with the first bore.

13. The kit of claim 12, wherein:
the pivot post comprises a receptor disposed opposite to the third bore and having a radial channel of a second arcuate length about an exterior surface of the pivot post; and
the retention pin of the implant is in communication with the radial channel, wherein range of rotational movement of the cage relative to the pivot post is controlled by the second arcuate length of the radial channel of the pivot post.

14. The kit of claim 13, wherein the first arcuate length of the channel of the cage is equal to the second arcuate length of the radial channel of the cage.

15. The kit of claim 11, wherein the opening in the second end of the cage has a first concave wall on the first lateral side of the cage extending from the lower surface of the upper shelf to the upper surface of the lower shelf, and a second concave wall on the second lateral side of the cage extending from the lower surface of the upper shelf to the upper surface of the lower shelf.

16. The kit of claim 15, wherein the first concave wall is longitudinally offset from the first and second edges a first offset distance, and the second concave wall is longitudinally offset from the first and second edges a second offset distance, the second offset distance less than the first offset distance.

17. The kit of claim 16, wherein the cage of the implant further comprises:
a first arcuate wall groove in the first concave wall; and
a second arcuate wall groove in the second concave wall.

18. The kit of claim 11, further comprising a medial cavity extending through the cage from the upper side to the lower side.

19. A method of implanting an impacted blade implant comprising the steps of:
providing an implant comprising:
a cage having an upper side, a lower side opposite to the upper side, a first lateral side, a second lateral side opposite to the first lateral side, a first end, a second end opposite the first end, an opening in the second end defining an upper shelf extending longitudinally from the upper side and a lower shelf extending longitudinally from the lower side, the upper shelf having a first edge and a lower surface, the lower shelf having a second edge and an upper surface, a first bore in the upper side adjacent the upper shelf and extending axially from the upper side to the lower surface, a second bore in the second lateral side, a lower groove in the upper surface of the lower shelf adjacent the second edge, an upper groove in the lower surface of the upper shelf adjacent the first edge, the lower groove and the upper groove axially offset from one another and forming a channel;
a pivot post disposed in the first bore of the cage, the pivot post having a central axis and a third bore in a radial side thereof that extends inward; and a retention pin received in the second bore in the second lateral side of the cage and in contact with the pivot post to constrain the cage to a range of rotation about the post and along the channel;

providing an insertion instrument for installing the implant, the insertion instrument comprising:

a handle having a proximal end and a distal end;

a frame having a proximal end and a distal end, the proximal end of the frame attached to the distal end of the handle;

a hollow shaft having a proximal end, a distal end, a first lateral side, and a second lateral side, the proximal end of the shaft attached to the distal end of the frame;

a first controller longitudinally movably disposed on the proximal end of the hollow shaft;

a rod having a proximal end and a distal end, the rod extending through the hollow shaft wherein the distal end extends from the open distal end of the hollow shaft and is configured to engage and disengage the third bore of the pivot post;

a second controller coupled to the rod, wherein rotation of the second controller moves the rod to couple or detach the end of the rod from the pivot post;

a first bar having a proximal end and a distal end, the proximal end of the first bar attached to the first controller whereby longitudinal movement of the second controller moves the first bar relative to the hollow shaft to extend and retract the distal end of the first bar to change the angular position of the attached cage through rotation of the cage about the pivot post;

a second bar disposed on and stationary relative to a second lateral side of the hollow shaft; and a protrusion situated on a distal face of the distal end of the insertion instrument adjacent the stationary second bar; and guiding the implant into a space using the insertion instrument.

* * * * *